United States Patent [19]

Makovec et al.

[11] 4,179,475

[45] Dec. 18, 1979

[54] OLEFIN FEED IN HF ALKYLATION OF ISOPARAFFIN WITH OLEFIN

[75] Inventors: Donald J. Makovec; Donald M. Haskell, both of Bartlesville, Okla.

[73] Assignee: Phillips Petroleum Company, Bartlesville, Okla.

[21] Appl. No.: 905,073

[22] Filed: May 11, 1978

[51] Int. Cl.² .............................................. C07C 3/54
[52] U.S. Cl. ................................................. 585/714
[58] Field of Search ...................... 260/683.48, 683.49, 260/683.43

[56] References Cited

U.S. PATENT DOCUMENTS

| 3,080,438 | 3/1963 | Sailors | 260/683.48 |
| 3,515,770 | 6/1970 | Tregilgas | 260/683.48 |
| 3,607,970 | 9/1971 | Borst, Jr. | 260/683.48 |
| 3,778,489 | 12/1973 | Parker et al. | 260/683.48 |
| 3,780,131 | 12/1973 | Sobel | 260/683.48 |
| 3,787,518 | 1/1974 | Anderson | 260/683.48 |
| 3,911,043 | 10/1975 | Anderson | 260/683.48 |
| 3,925,501 | 12/1975 | Putney et al. | 260/683.48 |

Primary Examiner—George Crasanakis

[57] ABSTRACT

In a conventional reactor into which at one end portion there are fed olefin, isoparaffin and HF acid, or other catalysts, and from which an alkylate containing product is passed to a phase separator or settling zone, there is added to the reactor to a downstream portion therein, beyond the original point of entry of the first olefin feed a second portion of olefin feed together with hydrocarbon phase recycled from the phase separator or settling zone.

3 Claims, 1 Drawing Figure

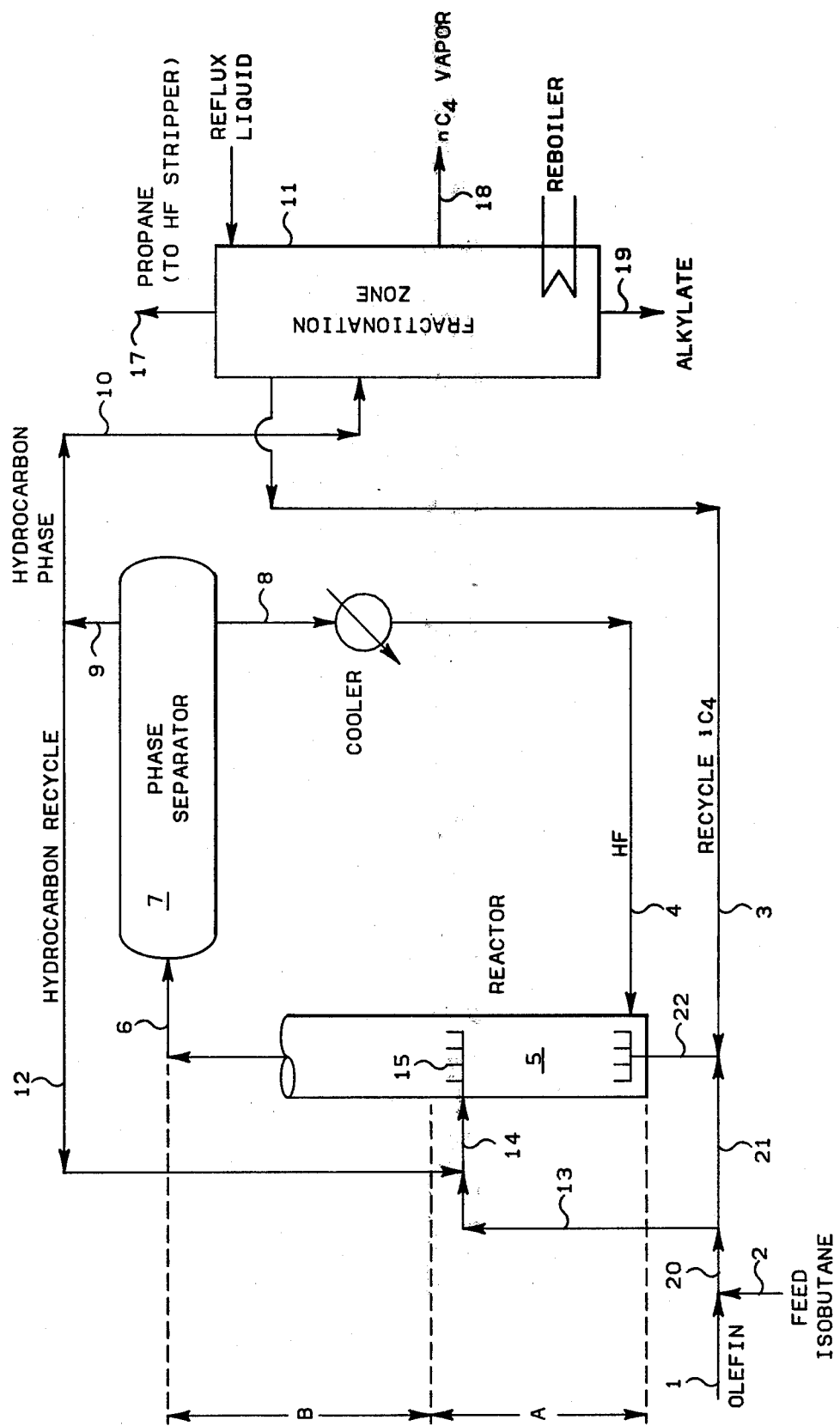

OLEFIN FEED IN HF ALKYLATION OF ISOPARAFFIN WITH OLEFIN

This invention relates to alkylation of hydrocarbons. In one of its aspects it relates to the alkylation of an isoparaffin and olefin. In a more specific aspect of the invention it relates to the catalytic alkylation of an isoparaffin with an olefin and to a manner of feeding the olefin to accomplish improved quality alkylate.

In one of its concepts the invention provides a process for the alkylation of an isoparaffin with an olefin in the presence of an acid catalyst, e.g., HF acid, in known manner, the addition of olefin being modified to add the same in at least two loci in the reaction zone there being added to the reaction zone at a point downstream from an original addition of olefin at least one further portion of olefin together with hydrocarbon phase recycled from the conventional phase separator or settling zone in which the reaction mass from the reacton zone is settled to separate hydrocarbon phase from acid phase. In another of its concepts the invention provides a process in which isobutane, olefin and HF acid are introduced to one end of a reaction zone and another portion of olefin, together with recycled hydrocarbon phase from the conventional phase separator, is added to said reaction zone at a point downstream from said end of said reaction zone. Still, in a further concept of the invention it is provided a process in which olefin is added to at least two space points within the conventional riser-reactor: a first portion being added together with isobutane and HF in substantially conventional manner at a first of said spaced points and a second portion being added to a second point downstream from said first of said spaced points, said second portion being added together with a substantial quantity of hydrocarbon phase recycled from the conventional phase separator or settling zone.

In actual representative pilot plant runs, on a comparative basis, adding all of the isobutane and all of the olefin to the lower locus of a riser reactor gave an alkylate of Research Octane with no tetraethyl lead of 92.7 whereas, according to the present invention with addition of at least 2 points spaced from each other, as described herein, an alkylate of Research Octane with no tetraethyl lead of 94.0 was obtained. At these rather high octane numbers an increase of 1.3 in the octane number is indeed pleasantly surprising. This is especially so when one considers the blending value of such alkylate and the reduction in attendant cost in energy which ensue to produce a conventional gasoline blend.

It is an object of this invention to provide an improved process for the alkylation of hydrocarbons. It is another object of the invention to provide a process for the alkylation of an isoparaffin with an olefin in the presence of an acid catalyst, e.g., HF acid. It is a further object of the invention to provide a process for the alkylation of isoparaffin with olefin in the presence of acid catalyst in which with the same amount of isoparaffin and olefin there can be obtained a very sizable increase in octane number. It is a further object of the invention to provide a process as herein described in which considerable fractionation costs are eliminated as will appear more fully hereinafter.

The disclosures of the following patents are now incorporated herein by reference: U.S. Pat. No. 3,080,438, Mar. 5, 1963, H. R. Sailors; 3,249,649, May 3, 1966, F. T. Sherk et al; 3,846,505, Nov. 5, 1974, Robert F. Anderson; 3,911,043, Oct. 7, 1975, Robert F. Anderson; and 4,008,292, Feb. 15, 1977, John P. James.

U.S. Pat. No. 3,080,438 shows in its drawing hydrocarbon recycle line 21.

Other aspects, concepts, objects and the several other advantages of the invention are apparent from a study of this disclosure, the drawing and the appended claims.

According to the present invention there is provided a process for the alkylation of an isoparaffin with an olefin in the presence of, say, hydrofluoric acid as in a conventional riser-reactor, or otherwise, wherein significantly improved octane number is obtained by introducing a first portion of the olefin feed together with isoparaffin and HF acid into one portion of a reaction zone through which there is flowing a mass of reactants and acid and then introducing downstream from said portion a further quantity of the olefin feed together with recycle hydrocarbon phase obtained from the phase separator or settling zone in which the reaction mass from the reaction zone is settled to separate hydrocarbon phase from acid phase.

As noted herein by operating according to the invention, a very significant increase in octane number has been obtained. Further, by recycle of hydrocarbon phase directly to the reactor the ratio of isoparaffin, i.e., isoparaffinic hydrocarbon to olefin at the second point of olefin feed is increased markedly within the equipment in which the recycle is effected without this quantity of constantly recycled hydrocarbon phase being subjected to otherwise necessary fractionation in the alkylate product fractionation zone.

It is within the scope of the invention and the claims as one skilled in the art in possession of this disclosure and having studied the same will understand to provide more than one additional olefin addition to, in effect, at least to an extent repeat the advantageous operation in the same or an additional reaction zone or vessel.

From the date given herein it will be seen that in the pilot plant the actual isoparaffin to olefin volume ratio at the reactor inlet was 12.6:1 whereas at the reactor midpoint to which the additional olefin, together with the recycle hydrocarbon phase, was added according to the invention was 35:1.

One skilled in the art and in possession of this disclosure having studied the same will recognize that by mere routine testing he can vary the isoparaffin or isobutane to olefin, e.g., propylene and/or butylenes and/or amylenes which are introduced to the reaction zone at the various places described herein. It is within the scope of the invention to add, together with the recycle hydrocarbon from a phase separator some isoparaffin, e.g., isobutane. Further the amount or proportion of olefin added to each portion of the reaction zone to which olefin is added can also be varied, the essential concept being that the olefin is added at least two spaced points and at least one of the points spaced downstream from another, where the olefin is added together with hydrocarbon phase recycled from the phase separator or settling zone.

Referring now to the drawing, which diagrammatically shows an operation according to the invention, and in which only those portions of apparatus are shown which are helpful to more fully describe the invention, total olefin is fed by 1, total feed isobutane is fed by 2, the admixture is passed by 20 and divided one portion by 21 and another portion by 13. The portion passed by 21 is blended with recycle isobutane 3 and passed by 22 to HF alkylation reactor 5 to which HF acid catalyst is added by 4. As shown, reactor 5 is a riser-reactor to which the described streams are fed at a bottom point or portion. The reacting mass rises upwardly through the reactor and is passed by 6 into phase separator 7. From phase separator 7 an acid phase is returned to the reactor by 8, cooler, and by 4. Supernatant hydrocarbon phase is passed by 9 and 10 to fractionation zone 11, for conventional fractionation. A portion of the hydrocarbon phase is taken from 9 by 12 and, together with olefin feed and feed isobutane fed by 13 is passed by 14 into reactor 5 at 15.

The manner of feeding the reactants to any portion of the riser-reactor can be varied. U.S. Pat. No. 3,281,213 issued Oct. 25, 1966, P. M. Waddill is illustrative of a type or manner of feeding reactant into an alkylation reaction zone. Its disclosure is incorporated herein by reference. It will be noted that the recycle isobutane fed to reactor 5 and which comes from fractionation zone 11 is significantly less, with consequent reduction of fractionation zone load, than would be required in the absence of hydrocarbon phase recycle from phase separator 7.

In fractionation zone 11 in addition to obtaining a recycle isobutane there are obtained the following streams and overhead propane, containing HF which is passed to an HF stripper, normal butane vapor which can be passed to isomerization to produce isoparaffin useful in the operation and the desired alkylate the respective streams being obtained at 17, 18 and 19.

Referring now to the tabular data obtained in actual pilot plant run it wil be noted that the length of the respective paths of travel of the reaction mass in the reaction zone are given. The ratio of these lengths in the actual run having been 1:1.

One skilled in the art will understand that the ranges which are given are estimated based upon plant experience and that ranges now given as at footnote b will depend upon plant design.

EXAMPLE

| | Ranges | Pilot Plant Run |
|---|---|---|
| (1) Total Olefin (a), bbls/hr. | (b) | 1.0 (c) |
| (2) Total Feed Isobutane (a), bbls/hr. | | 2.0 (c) |
| (20) Total of (1) and (2), bbls/hr. | (b) | 3.0 (c) |
| (13) Portion of (20) to Midpoint, bbls/hr. | (b) | 1.5 (c) |
| (21) Portion of (20) to Inlet, bbls/hr. | (b) | 1.5 (c) |
| (3) Recycle iC$_4$ (91.56 vol. % iC$_4$), bbls/hr. | (b) | 5.8 (c) |
| (12) Recycle hydrocarbon (68.2 vol % iC$_4$), bbls/hr. | (b) | 24.2 (c) |
| (22) Total Hydrocarbon to Reactor Inlet, bbls/hr. | (b) | 7.3 (c) |
| (14) Total Hydrocarbon to Reactor Midpoint, bbls/hr. | (b) | 25.7 (c) |
| (4) HF Catalyst to Reactor Inlet, bbls/hr. | (b) | 49.1 (c) |
| Composition, wt. % | | |
| HF | 85 to 95 | 92.2 |
| Water, | 0.5 to 4.5 | 3.8 |
| Acid Soluble Oils, | 0.5 to 5.0 | 0.5 |
| Hydrocarbons, | 2 to 6 | 3.5 |
| Volume Ratio of Streams 21/13 | 0.25:1 to 4:1 | 1:1 |
| Isobutane/Olefin Volume Ratios, | | |
| Reactor Inlet | 10:1 to 100:1 | 12.6:1 |
| Reactor Midpoint | 15:1 to 100:1 | 35:1 |
| Volume Ratio of Streams 3/21 | 2:1 to 100:1 | 3.9:1 |
| Volume Ratio of Streams 12/13 | 4:1 to 100:1 | 16.1:1 |
| Volume Ratio of HF/Total Hydrocarbon | 1:1 to 10:1 | 1.49:1 |
| Reactor (5) Temperature, °F., | 40 to 120 | 90 |

EXAMPLE-continued

| | Ranges | Pilot Plant Run |
|---|---|---|
| (Pressure to Maintain Liquid Phases) | | |
| Residence Time, seconds, (d), | | |
| Reactor Inlet Feed, (22) | 10 to 200 | 109 |
| Reactor Midpoint Feed, (14) | 10 to 200 | 45 |
| Zone A/Zone B Length Ratio | 0.5:1 to 30:1 | 1:1 |

(a) The olefin can be propylene and/or butylenes and/or amylenes. The plant run used propylene/mixed butylenes of 45/55 volume ratio. The isoparaffin can be isobutane and/or isopentane. The pilot plant run used isobutane. The recycle isobutane was 91.56 volume percent isobutane; the recycle hydrocarbon was 68.20 volume percent isobutane.
(b) Depends upon actual plant size.
(c) Actual pilot plant flows were scaled up by a factor of 200 for numerical simplicity.
(d) Residence times are based on total flow in the reactor-riser (5).

As noted, pilot plant operation set out above produced an alkylate of Research Octane with not tetraethyl lead of 94.0.

When operating at the same conditions, as set out hereinabove, but with adding all of the isobutane, and all of the olefin only to the lower locus of the reactor, so that the same total isobutane and same total olefin were equal to that total isobutane and total olefin used in the invention (same total isobutane to olefin ratio), the alkylate Research Octane with no tetraethyl lead was only 92.7.

Reasonable variation and modification are possible within the scope of the foregoing disclosure, drawing and the appended claims to the invention the essence of which is that in an alkylation of hydrocarbon, e.g., an isoparaffin with an olefin as in the presence of an acid, e.g., HF acid, the olefin is introduced at at least two spaced points in the reaction zone. At least one of the spaced points being downstream from another and that a later portion of introduced olefin is introduced together with hydrocarbon phase recycled from the phase separator or settling zone.

We claim:

1. The alkylation of an isoparaffin with an olefin in the presence of an acid catalyst which comprises introducing into one end of an elongated alkylation reaction zone a first portion of feed olefin together with a first portion of feed isoparaffin, together with recycled isoparaffin, at alkylation conditions for at least some reaction to take place and then downstream of said end introducing a second portion of said feed olefin, additional feed isoparaffin together with substantially all of a recycled hydrocarbon phase obtained in an ensuing settling zone, as hereinafter delineated, at alkylation conditions for additional reaction to take place, passing the effluent from said alkylation zone to said settling zone to separate a hydrocarbon phase from an acid phase, recycling the acid phase to said alkylation zone, separating said hydrocarbon phase into at least two portions, recycling a first portion of said hydrocarbon phase as said recycled hydrocarbon phase and passing another portion of said hydrocarbon phase to fractionation to withdraw an alkylate product.

2. An alkylation according to claim 1 wherein isoparaffin is alkylated with olefin in the presence of HF acid by first introducing a portion of the total olefin to be fed to said zone into one end of said zone together with isoparaffin and acid and at a point substantially spaced downstream from said first introduction, introducing said second portion of said olefin.

3. A process according to claim 2 wherein the isoparaffin is comprised substantially of isobutane and the olefin is at least one of propylene, butylenes and amylenes.

* * * * *